US005585277A

United States Patent [19]
Bowie et al.

[11] Patent Number: 5,585,277
[45] Date of Patent: Dec. 17, 1996

[54] SCREENING METHOD FOR IDENTIFYING LIGANDS FOR TARGET PROTEINS

[75] Inventors: James U. Bowie, Culver City, Calif.; Andrew A. Pakula, Lexington, Mass.

[73] Assignee: Scriptgen Pharmaceuticals, Inc., Medford, Mass.

[21] Appl. No.: 407,945

[22] Filed: Mar. 21, 1995

Related U.S. Application Data

[63] Continuation of Ser. No. 80,829, Jun. 21, 1993, abandoned.
[51] Int. Cl.$^6$ .................................................... G01N 33/53
[52] U.S. Cl. .................. 436/518; 436/501; 436/536; 435/4; 435/7.92; 435/23; 435/24
[58] Field of Search .................................. 435/23, 24, 4, 435/7.92; 436/501, 518, 536

[56] References Cited

PUBLICATIONS

Randall, L. K., *Science*, vol. 257, pp. 241–245 Jul. 10, 1992.
Grant, S. K., Biochemistry, vol. 31, pp. 9491–9501, 1992.
Tanigaki, N. et al., *Human Immunology*, vol. 36, pp. 119–127, 1993.
Zahnley, J. C., "Effects of Manganese and Calcium on Conformational Stability of Concanavalin A: A Differential Scanning Calorimetric Study", *J. Inorganic Biochem.* 15:67–78 (1981).
Grimaldi, S. et al., "Effects of Thyroxine Binding on the Stability, Conformation, and Fluorescence Properties of Thyroxine-Binding Globulin", *Biochem.* 21:145–151 (1982).
Pace, C. N. and T. McGrath, "Substrate Stabilization of Lysozyme to Thermal and Guanidine Hydrochloride Denaturation", *J. Biol. Chem.* 255:3862–3865 (1980).
Doyle, R. J. et al., "Stabilization of Concanavalin A by Metal Ligands", *Carbohydrate Res.* 46:111–118 (1976).
Casas–Finet, J. R. et al., "Mammalian Heterogeneous Ribonucleoprotein A1 and Its Constituent Domains", *J. Mol. Biol.* 229:873–889 (1993).
Merabet, E. K. et al., "Differential Scanning Calorimetric Study of 5-Enolpyruvoyl Shikimate-3-Phosphate Synthesis and its Complexes with Shikimate-3-Phosphate and Glyphosate . . . ", *Biochim. Biophys. Acta* 1161:272–278 (1993).
Fernandez–Ballester, G. et al., "Protein Stability and Interaction of the Nicotinic Acetylcholine Receptor With Cholinergic Ligands Studied by Fourier–Transform Infrared Spectroscopy", *Biochem. J.* 288:421–426 (1992).

Harrington, J. P., "Spectroscopic Analysis of the Unfolding of Transition Metal–Ion Complexes of Human Lactoferrin and Transferrin", *Int. J. Biochem.* 24:275–280 (1992).
Green, S. M. et al., "Roles of Metal Ions in the Maintenance of the Tertiary and Quaternary Structure of Arginase from *Saccharomyces cerevisiae*", *J. Biol. Chem.* 266:21474–21481.
Feng, Y. and S. G. Sligar, "Effects of Heme Binding on the Structure and Stability of *Escherichia coli* Apocytochrome $b_{562}$", *Biochem.* 30:10150–10155 (1991).
Parsell, D. A. and R. T. Sauer, "The Structural Stability of a Protein Is an Important Determinant of Its Proteolytic Susceptibility in *Escherichia coli*", *J. Biol. Chem.* 264:7590–7595 (1989).
Wagenhofer, M. et al., "Thermal Denaturation of Engineered Tet Repressor Proteins and Their Complexes with tet Operator and Tetracycline Studied by Temperature Gradient Gel electrophoresis", *Anal. Biochem.* 175:422–432 (1988).
Lapadat, M. A. and L. L. Spremulli, "Effect of Guanine Nucleotides on the Conformation and Stability of Chloroplast Elongation Factor Tu", *J. Biol. Chem.* 264:5510–5514 (1989).
Kuwajima, K. et al., "Influence of $Ca^{2+}$ Binding on the Structure and Stability of Bovine α–lactalbumin Studies by Circular Dichroism and Nuclear Magnetic Resonance Spectra", *Int. J. Peptide Protein Res.* 27:18–27 (1986).
Rosengart et al, "Heparin Protects Heparin–Binding Growth Factor–I From Proteolytic Inactivation In Vitro", Biochem. Biophys. Res. Commun., 152(1):432–440 (Apr. 15, 1988).
Nilsson et al. "Proper and Improper Folding of Proteins in the Cellular Environment", Annu. Rev. Mirobiol., 45:607–635 (1991).
Friguet et al. "Immunochemical Analysis of protein confirmation", pp. 287–310 in *Protein Structure A Practical Approach*, Creighton, ed., IRL Press (Oxford), 1989.

*Primary Examiner*—Toni R. Scheiner

[57] ABSTRACT

A novel method for screening chemical compounds, test ligands, for potential pharmaceutical effectiveness. The disclosed method identifies possible therapeutic test ligands by placing them in the presence of target proteins and determining the ability of test ligands to increase the ratio of folded target protein to unfolded target protein. This differs significantly from known methods of novel pharmaceutical testing in that the biochemical function of the target protein need not be known and, except for one of the five embodiments of the method, the existence of any known ligands of the target protein is unnecessary.

17 Claims, No Drawings

SCREENING METHOD FOR IDENTIFYING LIGANDS FOR TARGET PROTEINS

This is a continuation of application Ser. No. 08/080,829, filed Jun. 21, 1993 now abandoned.

BACKGROUND OF THE INVENTION

Pharmaceuticals can be developed from lead compounds that are identified through a random screening process directed towards a target, such as a receptor. Large scale screening approaches can be complicated by a number of factors. First, many assays are laborious or expensive to perform. Assays may involve experimental animals, cell lines or tissue cultures that are difficult or expensive to acquire or maintain. They may require the use of radioactive materials, and thus pose safety and disposal problems. These considerations often place practical limitations on the number of compounds that reasonably can be screened. Thus, those employing random screening methods are frequently forced to choose novel chemical compounds based on some prior knowledge suggesting the compounds are likely to be effective. This strategy limits the range of compounds tested, and many useful drugs may be overlooked.

Second, the specificity of many biochemical assays may overlook a wide variety of useful chemical compounds because the interactions between the ligand and the receptor protein are outside the scope of the assay. For example, many proteins have multiple functions, whereas most assays are capable of monitoring only one such activity. With such a specific assay, many potential pharmaceuticals are overlooked. Finally, in most existing biochemical screening approaches to drug discovery, the activity of the target protein must be defined. This requires that the system in question be well-characterized before screening can begin. Many new proteins are now identifiable through their DNA sequences. However, the specific functions of a protein encoded by a newly identified gene are usually not revealed by analysis of its DNA sequence. Consequently, biochemical screening for therapeutic drugs directed against many target proteins must await detailed biochemical characterization, a process which generally requires extensive research.

SUMMARY OF THE INVENTION

Disclosed herein is a novel method for determining the ability of a test compound, referred to as a test ligand, to bind a protein or protein complex of interest, referred to as a target protein. The method of the present invention is useful for identifying a ligand of a target protein and is particularly useful for screening test ligands to identify a ligand which binds a target protein such as a protein which is associated with a condition or disease or which participates in physiologic regulation. Thus, the present method is useful to identify a ligand which can be used therapeutically (i.e., for diagnosing, preventing or treating a condition or disease) or a ligand which can be used to regulate physiological function or which can serve as a lead compound for identification of a therapeutically useful compound. Through the present method, a ligand which binds a target protein is identified; such a ligand can then be further assessed, if needed, for its therapeutic effectiveness, as well as its safety, using known methods. A ligand for a target protein is identified by the present method by combining (incubating) a test ligand with a target protein, under conditions chosen to cause the protein to exist in an appropriate ratio of its folded and unfolded states in the case of a protein which unfolds reversibly or to cause the protein to unfold at an appropriate rate, in the case of a protein which unfolds irreversibly. Appropriate ratios and rates are dependent on assay conditions and are determined empirically for binding of the target protein to a ligand of the target protein. If the test ligand binds the target protein (i.e., if the test ligand is a ligand for the target protein), the target protein (i.e., the target protein to which the test ligand binds) remains in its folded state (does not unfold). Thus, for a protein which unfolds reversibly, if the test ligand-target protein mixture contains a ligand for the target protein, the relative amount of folded target protein is higher than is the case if the test ligand-target protein mixture does not contain a ligand for the target protein (i.e., the relative amount of folded target protein is higher in the presence of ligand than in its absence). Thus, if a test ligand is a ligand for a target protein, the ratio of folded target protein to unfolded target protein is greater than the corresponding ratio if the test ligand does not bind the target protein (is not a ligand). In the case of a protein which unfolds irreversibly, the rate of unfolding is slower if the target ligand-target protein mixture contains a ligand than if it does not. After a given time of incubation, the ratio of folded protein to unfolded target protein is greater than the corresponding ratio of target ligand does not bind the target protein.

The disclosed method relies on the principle that proteins generally exist as a mixture of folded and unfolded states, and continually alternate between the two states. Proteins may also unfold irreversibly. For example, proteins in solution and proteins covalently linked to a solid phase can undergo such interconversion. For reversibly unfolding, the ratio of folded to unfolded forms of a specific protein remains constant in a given set of conditions. When a test ligand binds to the folded form of a target protein (i.e., when the test ligand is a ligand of the target protein), the target protein molecule bound by the ligand remains in its folded state. Thus, the extent to which folded target protein is present is greater in the presence of a test ligand which binds the target protein (i.e., in the presence of a ligand) than in the absence of a ligand. Binding of the ligand to the target protein can be determined by any method which distinguishes between the folded and unfolded states of the target protein. For irreversible unfolding, ligan binding will slow the observed rate of unfolding. Thus, after an appropriate period of incubation of target protein and target ligand, binding of ligand to the target protein can be determined by any method which distinguishes between the folded and the unfolded target protein.

Binding to a given protein is a prerequisite for pharmaceuticals intended to modify directly the action of that protein. Thus, if a test ligand is shown, through use of the present method, to bind a protein which reflects or affects the etiology of a condition, it is a strong indication of the potential ability of the test ligand to alter protein function and to be an effective pharmaceutical or lead compound for the development of such a pharmaceutical. The method of the present invention thus provides an initial screen by which ligands (agents which bind a target protein) are identified; they can be further analyzed using known methods.

This method provides an inexpensive, quick, and efficient means to determine the ability of a large array of ligands to bind their respective target protein or proteins. Test ligands can be tested individually or as a component of a mixture and can be combined with one target protein or a mixture of target proteins. Binding of test ligand to target protein can be determined as described herein.

The fact that the present method is based on properties (the occurrence of folded and unfolded states and unfolding or alternation between the two states) common to most proteins gives it widespread application. Its rapidity and simplicity allow for large scale systematic screening of test ligands to determine their ability to bind a target proteins of interest.

DETAILED DESCRIPTION OF THE INVENTION

As described herein, the present invention relates to a method of identifying a ligand that binds a target protein, particularly a ligand which binds a target protein associated with or causative of a disease or condition and which is, thus, useful for diagnosing, preventing or treating the disease or condition. A ligand identified by the present method can also be one which is used in a purification or separation method, such as a method which results in purification or separation of the target protein from a mixture. The present invention also relates to ligands identified by the present method and their therapeutic uses (for diagnostic, preventive or treatment purposes) and uses in purification and separation methods.

As used herein, the term "test ligand" refers to an agent, which can be a compound, molecule or complex, which is being tested for its ability to bind to a target protein, such as a protein or-protein complex known to be associated with or causative of a disease or condition in a living organism, such as a vertebrate, particularly a mammal and even more particularly a human. Since binding of a ligand to its target protein must occur for the ligand to have a direct effect on the target protein, binding as indicated by the present assay method is a strong indication of the therapeutic potential of a ligand identified as described herein.

A test ligand which can be assessed by the present method can be virtually any agent, including, but not limited to, metals, polypeptides, proteins, lipids, polysaccharides, polynucleotides and small organic molecules. A test ligand which is shown to bind a target protein is referred to as a ligand complex mixtures of substances, such as natural product extracts, which include more than one test ligand can be tested and if there is a positive response (i.e., if binding to the target protein occurs), the ligand which bound the target protein can be purified from the mixture prior to further assessment of its therapeutic potential.

As used herein the term "target protein" refers to a polypeptide, protein or protein complex for which identification of a ligand or binding partner is desired, such as a polypeptide or protein that is known or believed to be involved in the etiology of a given disease, condition or pathophysiological state, or in the regulation of physiological function. It is not necessary that the protein's biochemical function has been specifically identified for the present method to be used to identify a ligand for the target protein. It is, of course, possible to carry out the method using a target protein whose role in the etiology of a disease or condition or in regulation of a physiological function is known. The target proteins can be, but are not limited to, receptors, oncogene products, tumor suppressor gene products, viral proteins, or transcription factors, either in purified form or as part of a complex mixture of proteins and other compounds. Further, target proteins can be, for example, wild type proteins, mutated or altered proteins (e.g., proteins changed in such a manner that they are less stable than the corresponding wild type protein) or proteins to which another component (e.g., a sequence of amino acids which facilitates purification) has been added.

In the present method, a test ligand is combined with a target protein for which a ligand (i.e., an agent which binds the target protein) is to be identified. The resulting combination is a test ligand-target protein combination or test combination. In general, the test ligand is present in excess molar amounts, relative to the target protein. The present method can be carried out in solution or, in some embodiments of the method, the target protein can be present on a solid phase (e.g., linked covalently through a linker or otherwise to a bead). The test ligand and target protein are combined under conditions (e.g., temperature, pH, salt concentration, time) appropriate for binding of the target protein to a ligand. In addition, conditions under which test ligand and target protein are combined are generally such that, for target proteins that unfold reversibly, a substantial fraction of target protein is present in the absence of the test ligand in the unfolded form, although the fraction can vary, depending on the detection method used. In the case of target proteins which unfold irreversibly, conditions are generally such that the target protein unfolds at a substantial rate in the absence of ligand. These conditions are chosen to ensure that the target protein unfolds to an appropriate extent; thus, the observed signal (e.g., digestion by a protease; binding to antibody, chaperonin or surface) can be measured conveniently. If too little target protein is unfolded, the observed signal will occur at too low a level or rate to be conveniently measured. For each test ligand-target protein combination assessed, the conditions under which the present method is carried out will be determined empirically, using known methods. Such conditions include reaction temperature and the chaotropic agent(s) or denaturant(s) used. The temperature at which the method is carried out is determined by the target protein being used and can be determined empirically using known methods. To adjust or optimize the fraction of unfolded target protein, denaturing conditions may be required for some target proteins. Such denaturing conditions might include the use of elevated temperatures, the addition of protein denaturants (e.g., urea, guanidine) to the incubation mixture or use of both. In addition, the stability of some target proteins might be adjusted through engineering destabilizing or stabilizing amino acid substitutions in the target protein. The test ligand and target protein are combined, maintained under appropriate conditions and for sufficient time for binding of the target protein to a ligand. The time necessary for binding of target protein to ligand will vary depending on the test ligand, target protein and other conditions used. In some cases, binding will occur instantaneously (e.g., essentially simultaneous with combination of test ligand and target protein), while in others, the resulting test ligand-target protein combination is maintained for a longer time before binding is detected. In the case of target proteins which unfold irreversibly, the rate of unfolding must also be taken into consideration in determining an appropriate time for binding of test ligand. Binding of a test ligand to the target protein is assessed in one of several ways: by determining the extent to which folded target protein is present in the test ligand-target protein combination; by determining the extent to which unfolded target protein is present in the test ligand-test protein combination or by determining the ratio of folded target protein to unfolded target protein in the combination. That is, the difference between the amount of folded target protein, the amount of unfolded target protein or the ratio of folded target protein to unfolded target protein in the presence of the test ligand and in its absence is determined. If a test ligand binds the target protein (i.e., if the test ligand is a ligand for the target protein), there will be more folded target protein and less unfolded target protein (and, thus, a higher ratio of folded to unfolded target protein and a lower ratio of unfolded to folded target protein) than is present in the absence of a test ligand which binds the target protein. It is not necessary to determine the quantity or fraction of an folded and unfolded target protein. It is only necessary to know that there is a difference in the amount of folded or unfolded protein (a change in equilibrium of the two forms) in the presence and absence of a ligand or a change in the rate of unfolding. This difference can be determined by comparing the extent to which folded and/or unfolded target protein is present in a test combination (test ligand-target protein combination) With the extent to which they are present in a control combination (target protein in the absence of test ligand). Alternatively, for reversible unfolding, the difference between the extent to which the two forms occur in the absence of a test ligand can be assessed by determining their occurrence initially (e.g., prior to addition of a test ligand to a solution of target protein or to solid support-bound test protein) and then after the test ligand has been combined with the target protein under conditions appropriate for target protein-ligand binding to occur. In either case, determination of the two forms of target protein can be carried out using a variety of known methods, which are described below. A test ligand which is shown by the present method to bind a target protein is referred to as a ligand of the target protein.

Methods for Determining the Presence of Folded Target Protein

There are numerous methods by which detection of binding of a test ligand to a target protein (and, thus, by which identification of a ligand of the target protein) can be carried out. Useful methods are those by which the folded target protein can be distinguished from unfolded target protein. The methods described below are some of the means by which this can be done. In each case, the detection method is carried out on a test combination (test ligand-target protein combination) after sufficient time has passed for binding of a target protein to its ligand and on a control combination (which is the same as the test combination except that no test ligand is present). A summary of the results of the methods described is presented in the Table.

Determining Ligand Binding Using Proteolysis

In one embodiment of the present method, binding of test ligand to target protein is detected through the use of proteolysis. In this embodiment, a protease which acts preferentially upon unfolded target protein is combined with the test ligand-target protein combination (test combination) and the resulting test combination-protease mixture is assayed after an appropriate period of incubation, using one of the methods described in detail below, to determine the difference between intact or degraded target protein in the presence and in the absence of the test ligand. An identical assay is performed on a test ligand-target protein combination and on a control combination and results of the two assays are compared. More intact protein or less degraded protein in the test combination than in the control combination indicates that the test ligand has bound the target protein and, thus, indicates that the test ligand is a ligand of the target protein. Similarly, a higher ratio of intact target protein to degraded protein in the test combination than in the control indicates the test ligand is a ligand of the target protein.

A wide variety of proteases, such as trypsin, chymotrypsin, V8 protease, elastase, carboxypeptidase, proteinase K, thermolysin and subtilisin, can be used in this embodiment. It is only necessary that the protease used be able to act upon (hydrolyze the peptide bonds of) the target protein used under the chosen incubation conditions and that this action be preferentially directed toward the unfolded form of the protein. To avoid interference by target ligands which directly inhibit the protease, more than one protease can be used simultaneously or in parallel assays.

In order to be efficiently digested the peptide bonds, the peptide substrate—the target protein—must have access to the enzyme active site of the chosen protease. Because the atoms in a folded protein molecule are tightly packed, the majority of the susceptible peptide bonds are sterically blocked from entering a protease active site when the protein is in the folded state. In the unfolded state, the peptide bonds are more exposed and are therefore relatively more susceptible to protease action.

Consequently, the addition of a test ligand which binds the folded target protein, stabilizing it in the protease-resistant form, changes the rate of proteolysis. Thus, by incubating the test ligand with the target protein, adding a protease to preferentially degrade the unfolded proteins, and then employing an assay to quantify the intact or the degraded target protein, it is possible to ascertain whether the test ligand bound the target protein and, thus, is a ligand of the target protein, indicating that it is potentially therapeutically useful.

Alternatively, the protease may be intrinsic to the unpurified or partially purified target protein sample.

Determining Ligand Binding Through Detection of Surface Binding

In another embodiment of the present method, the propensity of unfolded proteins to adhere to surfaces is utilized. This embodiment relies on the fact that folded proteins are held in specific three dimensional arrangements and, thus, are not as likely as their unfolded counterparts to bind a surface. If a test ligand binds a target protein (i.e., is a ligand of the target protein), it will stabilize the folded form of the target protein. Thus, the ability of a test ligand to bind a target protein can be determined by assessing the extent to which target protein is bound to an appropriate solid surface in the presence and in the absence of the test ligand. The methods described in detail below can be used for this purpose.

In this embodiment, the target protein, a test ligand and a surface that preferentially binds unfolded protein are combined and maintained under conditions appropriate for binding of the target protein to a ligand and binding of unfolded target protein to the surface. There are numerous suitable surfaces for this purpose, including microtiter plates constructed from a variety of treated or untreated plastics, plates treated for tissue culture or for high protein binding, nitrocellulose filters and PVDF filters.

If a test ligand binds the target protein, more folded target protein and less unfolded target protein is present in the test ligand-target protein combination than is present in a comparable control combination. That is, in the presence of a test ligand that is a ligand for a target protein, less unfolded protein is available to bind a surface that preferentially binds unfolded protein than in the absence of a ligand for the target protein. Determination of the amount of surface-bound target protein or the amount of target protein remaining in solution can be carried out using one of the methods described below. If more target protein is not surface bound (i.e., if more target protein is in solution) in the presence of a test ligand than in the absence of the test ligand, the test ligand is a ligand of the target protein. The ratio of target protein in solution to surface-bound target protein is greater if a test ligand is a ligand for the target protein than if it is not. Conversely, the ratio of surface-bound target protein to target protein in solution is less if a test ligand is a ligand for the target protein than if it is not.

Determining Ligand Binding Using Antibody Binding

In a third embodiment, the extent to which folded and unfolded target protein are present and, thus, binding of test ligand to target protein, are assessed through the use of specific antibodies directed against only the unfolded state ("denatured-specific antibodies" or "DS antibodies") or only the folded state ("nature specific antibodies" or "NS antibodies"). When a target protein is in the folded state, and stabilized in that state by test ligand which is a ligand for the target protein, the DS antibody's apparent binding affinity will be reduced (Breyer, (1989) "Production and Characterization of Mono-clonal Antibodies to the N-terminal Domain of the Lambda Repressor", *J. Biol. Chem.*, 264(5):13348–13354) and that of the NS antibody will be enhanced. If DS antibody binding to target protein is less or if NS antibody binding is greater in the presence of a test ligand than in its absence the test ligand is a ligand for the target protein.

There are numerous methods known in the art for producing antibody that binds to a particular protein (Harlow, E. & D. Lane, ANTIBODIES: A LABORATORY MANUAL, Cold Spring Harbor Laboratory, 1988, incorporated herein by reference). To prepare antibody specific for the denatured state, animals can be immunized with a peptide from a region of the protein that is buried in the native state. If the structure of the protein is unknown, antibodies can be prepared against several peptides and then the antibodies can be screened for preferential binding to the denatured state. Antibody production is by standard techniques, such as the technique for production of mono-clonal antibodies described in detail in Zola, *Monoclonal Antibodies: A Manual of Techniques*, CRC Press, Inc., Boca Raton, Fla. (1987), incorporated herein by reference.

There are at least three basic methods by which DS or NS antibodies can be utilized to detect a ligand-induced change in the occurrence of folded target protein, the occurrence of unfolded proteins or the ratio of one to the other.

In one approach, a test solution containing the DS antibody directed against the unfolded target protein, the target protein, and the test ligand is incubated, such as in a microtiter plate coated with the denatured target protein or a peptide fragment thereof, under conditions appropriate for binding of the target protein with its ligand and binding of the DS antibody to unfolded target protein. A control solution, which is the same as the test solution except that it does not contain test ligand, is processed in the same manner as the test solution. By comparing the amount of antibody bound to the plate or the amount remaining in solution in the test and control solutions, the difference in target protein folding is detected. The amount of antibody bound to the plate or remaining in solution can be measured as described below.

In a second approach, a test solution containing the DS antibody, the test ligand, and the target protein is incubated in a plate coated with a second antibody, referred to as a solid phase antibody, which cannot bind to the target protein simultaneously with the DS antibody, and is specific for the target protein, but is either specific for the folded state ("native specific" or "NS antibody") or unable to differentiate between the native and denatured states ("non-differentiating" or "ND antibody"). The resulting test combination or solution is maintained under conditions appropriate for binding of the target protein with a ligand of the target protein and for binding of the antibodies to the proteins they recognize (are specific for). A control solution, which is the same as the test solution except that it does not contain test ligand, is processed in the same manner as the test solution. In both solutions, denatured (unfolded) target protein binds the DS antibody and is inhibited from binding the solid phase antibody. The ability of the test ligand to bind the target protein can be gauged by determining the amount of target protein that binds to the solid phase antibody in the test solution and comparing it with the extent to which target protein binds to the solid phase antibody in the absence of test ligand, which in turn reflects the amount of target protein in the folded state. The amount of target protein bound to the plate via the second antibody or remaining in solution can be detected by the methods described below. This approach may be used in a comparable manner with NS antibody as the in solution antibody and DS or ND antibody on the solid phase.

In a third approach, a test solution containing the target protein and the test ligand is incubated in a container, such as a microtiter well which has been coated with a DS or NS antibody and maintained under conditions appropriate for binding of target protein to its ligand and for binding of the antibody to target protein. Alternatively, the antibody can be present on the surfaces of beads. The ability of the test ligand to bind the target protein is gauged by determining the extent to which target protein remains in solution (unbound to the antibody) or on the solid surface (bound to the antibody), or the ratio of the two, in the presence and in the absence of test ligand. If the test ligand binds the target protein (is a ligand of the target protein), there will be less target protein bound to a DS antibody or more bound to an NS antibody (i.e., more target protein will be in solution in the case of DS antibody or less in solution for NS antibody) than is bound to the antibody in the control solution. In a further embodiment, the antibody can be present in solution and the target protein can be attached to a solid phase, such as a plate surface or bead surface.

Determining Ligand Binding Using Molecular Chaperones

In a fourth embodiment, molecular chaperones are used to determine binding of a test ligand to a target protein. Chaperones are a variety of protein that bind unfolded proteins as part of their normal physiological function. They are generally involved in assembling oligomeric proteins, in ensuring that certain proteins fold correctly, in facilitating protein localization, and in preventing the formation of proteinaceous aggregates during physiological stress. Hardy, (1991) "A Kinetic Partitioning Model of Selective Binding of Nonnative Proteins by the Bacterial Chaperone SecB", *Science* 251:439–443 These proteins have the ability to interact with many unfolded or partially denatured proteins without specific recognition of defined sequence motifs.

One molecular chaperone, found in *E. coli*, is SecB. SecB has a demonstrated involvement in export of a subset of otherwise unrelated proteins. Competition experiments have shown that SecB binds tightly to all the unfolded proteins tested, including proteins outside of its particular export subset, but does not appear to interact with the folded protein.

In this embodiment, a test solution containing the test ligand and the target is incubated on a microtiter plate or other suitable surface coated with molecular chaperones, under conditions appropriate for binding of target protein with its ligand and binding of the molecular chaperones used to unfolded target protein. The unfolded target protein in the solution will have a greater tendency to bind to the molecular chaperone-covered surface relative to the ligand-stabilized folded target protein. Thus, the ability of the test ligand to bind target protein can be determined by determining the amount of target protein remaining unbound, or the amount bound to the chaperone-coated surface, using the methods detailed below.

Alternatively, a competition assay for binding to molecular chaperones can be utilized. A test solution containing purified target protein, the test ligand, and a molecular chaperone can be incubated in a container, such as a microtiter well coated with denatured (unfolded) target protein, under conditions appropriate for binding target protein with its ligand and binding of the molecular chaperones to unfolded target protein. A control solution which is the same as the test solution except that it does not contain test ligand is processed in the same manner. Denatured target protein in solution will bind to the chaperonin and, thus, inhibit its binding to the denatured target protein bound to the container surface (microtiter well surface). Binding of a test ligand to target protein will result in a smaller amount of unfolded target protein, and, thus, more chaperones will be available to bind to the solid-phase denatured target protein than is the case in the absence of binding of test ligand. Thus, binding of test ligand can be determined by assessing chaperones bound to the surface or in solution in the test solution and $i_D$ the control solution and comparing the results. Binding of chaperone to solid-phase denatured target protein to a greater extent in the test solution than in the control solution is indicative of test ligand-target protein binding (i.e., is indicative of identification of a ligand of the target protein). In this assay, the molecular shaperones are generally not provided in excess, so that competition for their binding can be measured.

Alternatively, test solution containing the target protein, the test ligand and a molecular chaperone can be incubated in a container, such as a microtiter well, whose surface is coated with antisera or a monoclonal antibody specific for the folded target protein (NS antibody) and unable to bind the target protein bound to the chaperone. Unfolded target protein will bind chaperone in solution and thus be inhibited from binding the solid phase antibody. By detecting target protein in the solution or bound to the well walls and comparing the extent of either or both in an appropriate control (the same combination without the test ligand), the ability of the test ligand to bind target protein can be determined. If the test ligand is a ligand for the target protein, more target protein will be bound to the antisera or monoclonal antibody bound to the container surface in the test solution than in the control solution. Conversely, less target protein will be present unbound (in solution) in the test solution than in the control solution. Detection and comparison of bound target protein, unbound target protein or a ratio of the two in the test solution and control solution indicate whether the test ligand is a ligand of the target protein or not.

Determining Ligand Binding Using Differential Binding to an Immobilized Ligand

The higher the fraction of protein in the folded form, the greater the amount of protein that is available to bind to a ligand that binds exclusively to the folded state. Consequently, if a protein has a known ligand, it is possible to increase the binding of the protein to the known ligand by adding a ligand that binds another site on the protein. In this approach, a ligand known to bind to the target protein is immobilized on a solid substrate. A solution containing the target protein is then added, along with test ligand or ligands. An increase in the amount of target protein that binds to the immobilized ligand relative to an identical assay in the absence of test ligand indicates that the test ligand binds the target protein. The amount of target protein bound to the solid substrate can be assessed by sampling the solid substrate or by sampling the solution, using the detection methods outlined below.

Determining Ligand Binding Through Measurements of Protein Aggregation

For proteins that unfold irreversibly, unfolded protein often forms insoluble aggregates. The extent of protein aggregation can be measured by techniques outlined below such as light scattering, centrifugation, and filtration. In this approach, target protein and test ligand are incubated and the amount of protein aggregation is measured over time or after a fixed incubation time. The extent of protein aggregation in the test mixture is compared to the same measurement for a control assay in the absence of test ligand. If a test ligand binds a target protein, the rate of unfolding of target protein will be lower than in the absence of test ligand. For measurements over time, the rate of increase of unfolded protein and hence of aggregated protein will be lower if the test ligand is a ligand for the target protein than if it is not. For measurements at a fixed time, there will be less unfolded protein add therefore less aggregated protein if the test ligand is a ligand for the target protein than if it is not. Thus, the ability of a test ligand to bind a target protein can be determined by assessing the extent of protein aggregation in the presence and absence of test ligand.

TABLE

DETERMINING FOLDED AND UNFOLDED TARGET PROTEIN

| Monitoring Method Used | Result Observed If Test Ligand Binds Target Protein |
| --- | --- |
| Proteolysis | |
| Protease which preferentially hydrolyzes unfolded target protein is used | More intact target protein/ less degraded protein in test combination than in control combination |
| Surface Binding | |
| Surface which preferentially binds unfolded target protein is used | More target protein unbound (in solution)/less bound to surface in test combination than in control combination |
| Antibody Binding | |
| DS antibody in solution/ unfolded target protein or peptide fragment thereof on surface | More DS antibody bound/less unbound to unfolded target protein or peptide fragment thereof on surface in test combination than in control combination |
| DS antibody in solution/ antibody that recognizes folded target protein on surface | More target protein bound/ less unbound to antibody on surface in test combination than in control combination |
| NS antibody in solution/ antibody that recognizes folded target protein on surface | Less target protein bound/ more unbound to antibody on surface in test combination than in control combination |
| DS antibody on surface | Less target protein bound to DS antibody on surface/more in solution in test combination than in control combination |
| NS antibody on surface | More target protein bound to NS antibody on surface/less in solution in test combination than in control combination |

TABLE-continued

DETERMINING FOLDED AND UNFOLDED TARGET PROTEIN

| Monitoring Method Used | Result Observed If Test Ligand Binds Target Protein |
|---|---|
| Molecular Chaperones | |
| Chaperone on surface | Less target protein bound to chaperone on surface/more in solution in test combination than in control combination |
| Competition Assay | |
| Unfolded target protein on solid phase, target protein in solution | More chaperone bound to unfolded target protein on solid phase/less in solution in test combination than in control combination |
| Chaperone in solution/ antibody which recognizes folded target protein on surface | More target protein bound to surface-bound antibody/less bound to chaperone in solution in test combination than in control combination |
| Differential Binding to Immobilized Ligand | |
| Target protein in solution, known ligand of target protein attached to surface | More target protein bound/ less unbound to surface-bound ligand in test combination than in control combination |
| Protein Aggregation | |
| Formation of aggregated protein by irreversible protein unfolding | Less aggregated protein (lower rate of formation of aggregated protein)/more soluble protein in test combination than in control |

Detection Methods

Methods known in the art to detect the presence or absence of protein, small peptides or free amino acids can be used in the present method. The method used will be determined by the product (proteins, peptides, free amino acids) to be detected. For example, techniques for detecting protein size can be used to determine the extent of proteolytic degradation of the target protein. Radio-labeling, fluorescence labeling, and enzyme-linked labeling can detect the presence or absence either in solution or on a substrate by measurement of radioactivity, fluorescence or enzymatic activity. Immunologic methods can detect the presence or absence of a known target protein in solution or on a substrate such as by binding of an antibody specific for that protein.

Gel electrophoresis can be used to detect the presence or absence of protein, and can further be used to detect the size of the protein. This latter method is especially useful in conjunction with proteolysis, as the presence of a greater amount of undigested target protein in the test combination than in the control combination indicates that the target protein was protected from proteolysis by binding to ligand. Some examples of useful detection techniques are described below. These techniques can be applied to samples taken from either the solution or the solid phase after incubation, as described above in section I.

In the following, primary antibody refers to antibody that binds the target protein specifically. Secondary antibody refers to antibody that binds to the primary antibody. Enzyme-linked, radiolabeled and fluorescence-labeled secondary antibodies are commercially available, or can be prepared by standard methods known in the art.

Methods for Detecting Target Protein in Solution

The target protein may be subjected to denaturing polyacrylamide gel electrophoresis followed by non-specific in the test combination than in the control combination indicates that the target protein was protected from proteolysis by binding to ligand. Some examples of useful detection techniques are described below. These techniques can be applied to samples taken from either the solution or the solid phase after incubation, as described above in section I.

In the following, primary antibody refers to antibody that binds the target protein specifically. Secondary antibody refers to antibody that binds to the primary antibody. Enzyme-linked, radiolabeled and fluorescence-labeled secondary antibodies are commercially available, or can be prepared by standard methods known in the art.

Methods for Detecting Target Protein in Solution

The target protein may be subjected to denaturing polyacrylamide gel electrophoresis followed by non-specific protein detection, such as Coomassie or silver staining. With the electrophoretic method, multiple target proteins can be analyzed in a single lane as long as they are of sufficiently different size to be resolved from one another. For this method of detection, the target protein may be present in a mixture of proteins, but in order that it will not be obscured by other proteins in the sample, it must represent a sufficiently large fraction of the total protein in the sample and must have an electrophoretic mobility such that it can be resolved from other proteins. Alternatively, proteins separated by denaturing polyacrylamide gel electrophoresis may be transferred to a membrane support (eg., nitrocellulose) and target protein detected with labeled (e.g., radiolabeled, enzyme-linked, fluorescence labeled, etc.) primary antibody or primary antibody followed by labeled secondary antibodies. For this method, the target protein may be present in a mixture of proteins.

Alternatively, the target protein may be detected by transfer of protein solution to a container, such as a well of a high protein-binding microtiter dish, where it becomes bound to the surface of the well. The remaining protein binding sites on the well can then be blocked by incubation with a solution containing proteins different from the target protein. To determine target protein bound to the well, primary antibody can be added and any unbound primary antibody washed off. The bound primary antibody can then be detected by adding a solution of labeled secondary antibodies. After washing off the secondary antibody, the amount of secondary antibody bound, which reflects the amount of target protein originally in solution, can be determined by observing the label through methods such as using an enzyme assay, fluorescence detection, or by determination of the radioactivity in the well. Alternatively, if the primary antibody has been labeled, then the secondary antibody step can be omitted and presence of label determined directly.

If the target protein to be measured is complexed with chaperone protein or antibody as a consequence of the method used for distinguishing folded and unfolded protein, then the primary antibody used for quantification must be chosen such that it can bind to the target protein in the context of this preformed complex. This method may be used for target proteins that are present in a mixture of proteins; however, the concentration of target protein in the mixture must be sufficiently high so that target protein binding to the wells is sufficient to result in an adequate signal.

In another approach, the amount of target protein in solution is determined by a primary antibody competition assay. The wells of a container, such as a high protein-binding microtiter dish, are first coated with purified target protein and blocked with non-target protein. The protein solution is then transferred to the coated well and primary antibody is added. The amount of target protein in the sample is measured by its ability to inhibit the binding of the primary antibody to the plate-bound protein. After washing the well to remove primary antibody remaining in solution, the bound primary antibody can be assayed in one of two ways. As for the previous methods, primary antibody can be labeled and directly detected, or a labeled secondary antibody can be used and detected. This method is suitable for target protein that is present in a mixture of proteins. Again, the choice of primary antibody must take into consideration whether the target protein is complexed with another protein.

If the target protein can be radiolabeled, linked to an enzyme with a readily measurable enzymatic activity or labeled in some other way, another type of competition assay can be performed. In this assay, the ability of the solution being tested to inhibit the binding of the labeled target protein to primary antibody can be measured. The target protein-specific antibody can be bound to a solid support. For example, the wells of a high-protein binding microtiter plate can be coated with primary antibody. The amount of labeled target protein bound to the well or free in solution can be determined by scintillation counting, enzymatic assay, or other appropriate assay. Alternatively, primary antibody, labeled target protein and the test solution can be mixed and then the antibody and any bound protein can be precipitated from solution by such means as an antibody binding protein like *Staphloccocus aureus* protein A attached to an insoluble particle. The amount of precipitated or soluble label can then be determined.

If the target protein that is labeled in some manner is used in the discrimination assay, the amount of label that has bound, has remained in solution, or has escaped proteolysis, can be measured. In the case of the proteolysis assay, intact, labeled protein would need to be separated from the labeled proteolysis products. This can be accomplished by the denaturing gel electrophoresis methods above, filtration, or precipitation such as with trichloroacetic acid. Alternatively, the wells of a high-protein binding microtiter plate can be coated with primary antibody, the test solution added, unbound protein washed off and label bound to the plate quantified. For example, if the protein were radiolabeled, the radioactivity remaining in the wells can be determined. If the target protein were enzyme-linked, then the enzyme activity remaining can be determined.

Alternatively, labeled target protein can be bound to specific antibodies in solution. The antibodies, along with any bound labeled target protein, can then be removed from solution by immunoprecipitation using precipitating antibodies or insoluble beads or fixed cells bearing secondary antibodies or other antibody-binding proteins such as *S. aureus* protein A. Target protein may then be measured by quantifying radioactivity or enzymatic activity. If the protein being tested has some measurable activity the amount of activity can be determined.

The presence of aggregated target protein in solution can be measured spectrophotometrically through measurements of light scattering or turbidity. Alternatively, to separate aggregated target protein from soluble target protein, centrifugation or filtration can be used. Aggregated protein will be precipitated by centrifugation and will be retained on filters after filtration. The precipitated protein, filter-bound protein, or protein remaining in solution can be measured by methods indicated above.

Methods for Detecting Antibody in Solution

In the following, test antibody refers to the antibody that binds the target protein specifically and whose concentration is to be measured. Secondary antibody has the same meaning as above except that secondary antibodies bind specifically to the test antibody.

The test antibody may be subjected to denaturing polyacrylamide gel electrophoresis followed by non specific protein detection, such as Coomassie or silver staining. Alternatively, proteins separated by denaturing polyacrylamide gel electrophoresis may be transferred to a membrane support (eg. nitrocellulose) and the test antibody detected with enzyme-linked or radiolabeled secondary antibodies.

The test antibody may also be detected by transfer of protein solution to a well of a high protein-binding microtiter dish where it becomes bound to the surface of the well. The remaining protein binding sites on the well can then be blocked by incubation with a solution containing non-antibody proteins. To quantify the amount of antibody bound to the well, a solution of labeled secondary antibodies can be added. After washing off the secondary antibody, the amount of secondary antibody bound can be determined by art appropriate method. Alternatively, if the test antibody has been labeled, then the secondary antibody step can be omitted and label determined directly.

The amount of test antibody in solution can also be detected by a target protein competition assay. The wells of a high protein-binding microtiter dish, can first be coated with test antibody and blocked with other protein. The solution containing the test antibody whose concentration is to be measured can then be transferred to the coated well and target protein added. The amount of test antibody in the sample can be measured by its ability to inhibit the binding of the target protein to the plate bound test antibody. After washing the well to remove the target protein remaining in solution, the bound target protein can be quantified Using one of the methods for detecting target protein bound to a solid substrate described in section C below.

If the test antibody is radiolabeled or labeled in some other way, another type of competition assay can be performed. In this assay, the ability of the solution being tested to inhibit the binding of the labeled test antibody to the target protein would be measured. The target protein can be bound to a solid support. For example, the wells of a high-protein binding microtiter plate can be coated with target protein. After washing out the unbound labeled test antibody, the amount of radiolabeled test antibody bound to the well can be determined by scintillation counting.

If the test antibody that is labeled in some manner is used in the discrimination assay, the amount of label remaining in solution can be detected directly.

Methods for Detecting Protein Bound to a Solid Substrate

If the target protein is labeled in some manner, the amount of target protein bound to a solid substrate can be determined directly. For example, if the target protein is radiolabeled, the amount of bound radioactivity can be determined. If the target protein is enzyme linked, then enzymatic activity can be determined.

If the target protein possesses some intrinsic activity, it may be possible to measure the amount of that activity bound to the solid substrate.

The amount of protein bound to a solid substrate can also be quantified by measuring the amount of primary antibody that binds to the solid surface via the protein after all non-specific protein binding sites have been blocked by incubation with high concentrations of non-target protein. If the primary antibody is labeled, the amount of primary antibody bound can be determined directly. Alternatively, a secondary, labeled antibody specific for the primary antibody can be employed to detect the amount of primary antibody bound to the bound target protein.

If the target protein is the only protein present on the solid substrate, it is possible to measure the amount of protein bound using some non-specific protein assay, such as the ninhydrin reaction. Ninhydrin undergoes a spectral shift upon reaction with peptide termini.

The target protein can be stripped from the solid substrate and then detected by any of the methods for detecting protein in solution described in section A above.

Methods for Detecting Antibody Bound to a Solid Substrate

If the test antibody is labeled in some manner, the amount of test antibody bound to the solid substrate can be determined directly. For example, if the test antibody is radiolabeled, the amount of bound radioactivity can be determined. If the test antibody is enzyme linked, then enzymatic activity can be determined.

If the test antibody bound to the solid substrate is not labeled in some manner, a second, radiolabeled or enzyme-linked antibody specific for the solid substrate bound antibody can be employed. The secondary antibody can be added and allowed to bind to the solid substrate bound antibody and then any unbound secondary antibody washed away. The amount of secondary antibody can then be quantified by appropriate methods.

The test antibody can be stripped from the solid substrate and then detected by one of the methods for detecting antibody in solution described in section B above.

The present invention is illustrated by the following examples, which are not to be seen as limiting in any way.

EXAMPLES

Example 1

Methotrexate Binding Protects Dihydrofolate Reductase (DHFR) From Proteolytic Digestion by Proteinase K The following were combined and incubated at 54° C. for 5 minutes: DHFR (100 µg/ml), Proteinase K (80 µg/ml), 0.1 $\underline{M}$ Tris-HCl [pH 7.5], and Methotrexate at $10^{-10}$ to $10^{-4}$ $\underline{M}$.

Samples were removed and undigested DHFR was quantified by ELISA as follows:

(a) Protease incubations were diluted 50 fold with Tris-buffered saline (TBS);

(b) 50 µl diluted samples were transferred to the wells of an ELISA plate and incubated 60 minutes at room temperature;

(c) the plate wells were thoroughly washed with TBS plus 0.1% Tween-20 (TBST);

(d) 50 µl anti-DHFR rabbit serum diluted 250 fold into TBST plus 5% nonfat dry milk was added to each well and incubated 30 minutes at room temperature;

(e) plate wells were washed as in (c) above;

(f) 50 µl of goat anti-rabbit IgG alkaline phosphatase conjugate diluted 500 fold in TBST plus 5% milk was added to each well and incubated 30 minutes at room temperature;

(g) plate wells were washed as in (c); and (h) 0.1 ml. of 1.0 mg/ml p-nitrophenylphosphate in 0.1% diethanolamine was added. Color development is proportional to alkaline phosphatase antibody conjugate bound.

The ELISA analysis showed that methotrexate protects DHFR from digestion at concentrations of $10^{-8}\underline{M}$ and higher. By the same methods, NADPH and dihydrofolate at concentrations of $10^{-5}$ and higher were shown to inhibit proteolysis of DHFR in separate experiments.

Example 2

Methotrexate, NADPH and Dihydrofolate Binding Protects Dihydrofolate Reductase (DHFR) From Proteolytic Digestion by Proteinase K in the Presence of a Mixture of Amino Acids The following were combined and incubated at 54° C. for 5 minutes: DHFR (2.1 µg/ml), Proteinase K (80µg/ml), 0.1 $\underline{M}$ Tris-HCl [pH 7.5], 10–5M of all 20 common amino acids and either 0 or 10–5M ligand. The ligands used were the inhibitor Methotrexate and the substrates dihydrofolate and NADPH.

Samples were removed and undigested DHFR was quantified by ELISA as follows:

(a) Protease incubations were diluted 50 fold with Tris-buffered saline (TBS);

(b) 50 µl diluted samples were transferred to the wells of an ELISA plate and incubated 60 minutes at room temperature;

(c) the plate wells were thoroughly washed with TBS plus 0.1% Tween-20 (TBST);

(d) 50 µl anti-DHFR rabbit serum diluted 250 fold into TBST plus 5% nonfat dry milk was added to each well and incubated 30 minutes at room temperature;

(e) plate wells were washed as in (c) above;

(f) 50 µl of goat anti-rabbit IgG alkaline phosphatase conjugate diluted 500 fold in TBST plus 5% milk was added to each well and incubated 30 minutes at room temperature;

(g) plate wells were washed as in (c); and (h) 0.1 ml. of 1.0 mg/ml p-nitrophenylphosphate in 0.1% diethanolamine was added. Color development is proportional to alkaline phosphatase antibody conjugate bound.

The ELISA analysis showed that methotrexate and the substrates protect DHFR from digestion relative to the absence of ligands that bind to DHFR. Thus, specific binding can be detected in the presence of a complex mixture of compounds that don't bind to the target protein.

Example 3

Methotrexate Binding Inhibits Binding of DHFR to Microtiter Plates

The following were combined in a volume of 60 µl and incubated in a Falcon 3072 "tissue-culture treated" microtiter plate at 20° or 47° C.: 100 ng DHFR, 50 mM Tris-Cl [pH 7.5], and Methotrexate $10^{-10}$ to $10^{-4}\underline{M}$.

50 µl of each sample Was then transferred to the wells of an ELISA plate, and the DHFR that remained in solution was quantified by ELISA as follows:

(a) The 50 µl samples were incubated for 60 minutes at room temperature;

(b) the plate wells were thoroughly washed with TBS plus 0.1% Tween-20 (TBST);

(c) 50 μl anti-DHFR rabbit serum diluted 250 fold into TBST plus 5% nonfat dry milk was added to each well and incubated 30 minutes at room temperature;

(d) plate wells were washed as in (c) above;

(e) 50 μl of goat anti-rabbit IgG alkaline phosphatase conjugate diluted 500 fold in TBST plus 5% milk was added to each well and incubated 30 minutes at room temperature;

(f) plate wells were washed as in (b); and (g) 0.1 ml. of 1.0 mg/ml p-nitrophenylphosphate in 0.1% diethanolamine was added. Color development is proportional to alkaline phosphatase antibody conjugate bound.

The ELISA analysis revealed that methotrexate inhibits DHFR binding to the Falcon 3072 plate at concentrations of $10^{-7}$ and above.

Example 4

Inhibition of Unfolded-Specific Antibody Binding (1) ELISA plates are coated by incubation for 60 minutes with the following mixture: 4 μg/ml irreversibly denatured target protein or peptide fragments thereof in Tris-buffered Saline 10 mM Tris-Cl [pH 7.5], 0.2M NaCl (TBS).

(2) The plates are washed 3 times with TBS plus 0.1% Tween-20 (TBST).

(3) The following mixture (total volume 50 μl) is incubated in the coated wells of the microtiter plate for 60 minutes:

(a) Antibody specific for the unfolded state of the target protein at a sufficient concentration to give 50% of maximal binding (in the absence of competing target protein).

(b) Target protein at a concentration sufficient to achieve 90% inhibition of antibody binding to the plate. The appropriate target protein concentration differs for each target protein. The concentration depends, in part, on the stability of the folded form of the target protein. In some cases it may be desirable to reduce the stability of the target protein by elevated temperature, inclusion of chemical protein-denaturing agents, or introduction of destabilizing amino acid substitutions in the target protein.

(c) $10^{-9}$ to $10^{-5}$M test ligands (d) 5% nonfat dry milk in TBST (4) The plates are washed 3 times with TBST.

(5) 50 μl of goat anti-IgG alkaline phosphatase conjugate at an appropriate dilution are added in TBST plus 5% nonfat dry milk and incubated for 30 minutes at room temperature.

(6) Plates are washed 3 times with TBST.

(7) 0.1 ml. of 1.0 mg/ml p-nitrophenylphosphate in 0.1% diethanolamine are added and the amount of color development recorded by means of an ELISA plate reader. ELISA analysis reveals more antibody bound to the plate when successful test ligand-target protein binding has occurred than in the absence of such binding.

Example 5

Inhibition of Chaperone Binding (1) ELISA plates are coated by incubation for several hours with 4 μg/ml chaperone in TBS.

(2) The plates are washed 3 times with TBST.

(3) The following mixture (total volume 50 μl) is then incubated in the coated wells of the microtiter plate for 60 minutes:

(a) Target protein at a concentration sufficient to saturate about 50% of the available binding sites present on the chaperone proteins. Denaturing conditions may be used in cases where the folded form of the target protein is otherwise too stable to permit appreciable binding to chaperones.

(b) $10^{-9}$ to $10^{-5}$ M test ligands in TBST (4) Aliquots of the well solutions are transferred to wells of a new ELISA plate and incubated for 60 minutes at room temperature.

(5) The plate wells are washed 3 times with TBST.

(6) 50 μl antibody specific for the target protein at the appropriate dilution in TBST, plus 5% nonfat dry milk, are added to each well and incubated 30 minutes at room temperature.

(7) The plate wells are washed 3 times with TBST.

(8) 50 μl of goat anti-rabbit IgG alkaline phosphatase conjugate at an appropriate dilution in TBST plus 5% nonfat dry milk are added to each well and incubated 30 minutes at room temperature.

(9) The plate wells are washed 3 times with TBST.

(10) 0.1 ml. of 1.0 mg/ml p-nitrophenylphosphate in 0.1% diethanolamine will be added. Color development (proportional to alkaline phosphatase antibody conjugate bound) is monitored with an ELISA plate reader.

ELISA analysis reveals target protein in the solution at higher concentration when test ligand-target protein binding has occurred than when it has not.

Example 6

Enhancement or Inhibition of Binding to a Known Ligand (1) The following mixture (total volume 50 μl) is incubated in the coated wells of the microtiter plate for 60 minutes:

(a) Ligand known to bind to the target protein, covalently attached to solid beads such as Sephadex. This ligand can be a small molecule or a macromolecule.

(b) Target protein at a concentration well below saturation of the ligand and such that only 10% of the protein binds to the ligand sites. The solution conditions are such that most of the target protein is present in the denatured state.

(c) $10^{-9}$ to $10^{-5}$M test ligands (d) in TBST plus necessary denaturant, such as urea.

(2) Aliquots of the well supernatant (free of beads) are transferred to wells of a new ELISA plate and incubated for 60 minutes at room temperature.

(3) The plate wells are washed 3 times with TBST.

(4) 50 μl antibody specific for the target protein at the appropriate dilution in TBST, plus 5% nonfat dry milk, are added to each well and incubated 30 minutes at room temperature.

(5) The plate wells are washed 3 times with TBST.

(6) 50 μl of goat anti-rabbit IgG alkaline phosphatase conjugate at an appropriate dilution in TBST plus 5% milk are added to each well and incubated 30 minutes at room temperature.

(7) The plate wells are washed 3 times with TBST.

(8) 0.1 ml. of 1.0 mg/ml p-nitrophenylphosphate in 0.1% diethanolamine are added. Color development (proportional to alkaline phosphatase antibody conjugate bound) is monitored with an ELISA plate reader.

ELISA analysis reveals lower concentration of target protein in the solution when successful test ligand-target protein binding has occurred.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method for rapid, large-scale screening to identify a ligand that binds to a predetermined target protein, comprising the steps (a) selecting as test ligands a plurality of compounds not known to bind to the target protein;

(b) incubating each of said test ligands and the target protein to produce a test combination;

(c) incubating the target protein in the absence of a test ligand to produce a control combination;

(d) treating the test and control combinations to cause the target protein in the control combination to unfold to a measurable extent;

(e) determining the extent to which the target protein occurs in the folded state, the unfolded state or both in the test combination and in the control combination;

(f) comparing the determination made in step (e) between the test and control combinations, wherein if the target protein is present in the folded state to a greater extent in the test combination than in the control combination, the test ligand is a ligand that binds to the target protein; and (g) repeating steps (b)–(f) with a plurality of said test ligands until a ligand that binds to the target protein is identified.

2. The method of claim 1, wherein in step (d), determining the extent to which target protein occurs in the folded state, the unfolded state, or both is carried out by a method selected from the group consisting of proteolysis, antibody binding, surface binding, molecular chaperone binding, differential binding to immobilized ligand and differential formation of aggregated protein.

3. The method of claim 2, wherein the determining step comprises the steps of:

(i) incubating the target protein, each of said test ligands and one or more proteases which preferentially degrade target protein in its unfolded state, whereby the target protein in its unfolded state is degraded preferentially; and (ii) measuring the fraction of the target protein degraded or the fraction of the target protein remaining in an intact state, wherein if the fraction of target protein remaining in the intact state in the test combination is greater than in the control combination, then the test ligand is a ligand that binds to the target protein.

4. The method of claim 2, wherein the determining step comprises the steps of:

(i) combining the target protein and each of said test ligands;

(ii) exposing the target protein and the test ligand mixture to a surface which preferentially binds unfolded target protein, whereby unfolded target protein binds to the surface; and (iii) determining the fraction of the target protein bound to the surface or the fraction of the target protein remaining unbound, wherein if the fraction of target protein remaining unbound is greater in the test combination, than in the control combination, the test ligand is a ligand that binds to the target protein.

5. The method of claim 2, wherein the determining step comprises the steps of:

(i) combining the target protein and each of said test ligands on a surface to which a known ligand of the target protein has been immobilized; and (ii) determining the fraction of the target protein bound to the surface or the fraction of the target protein remaining unbound wherein the fraction of target protein bound to the surface is greater in the test combination than in the control combination, the test ligand is a ligand that binds to the target protein.

6. The method of claim 2, wherein the determining step comprises using antibodies that distinguish between the folded form and the unfolded form of the target protein.

7. A method as in claim 6, wherein the determining step further comprises the steps of:

(i) coating a surface with the target protein in its unfolded state or with peptide fragments of the target protein;

(ii) incubating an antibody directed against the unfolded state of the target protein in the presence of both the target protein and each of said test ligands; and (iii) determining the amount of the antibody bound to or remaining unbound to the surface.

8. The method of claim 6, wherein the determining step comprises the steps of:

(i) coating a surface with a specific antibody directed against the denatured state of the target protein;

(ii) incubating the target protein in the presence of each of said test ligands on the surface; and (iii) determining the fraction of the target protein bound to or not bound to the surface.

9. The method of claim 6, wherein the determining step comprises the steps of:

(i) coating a surface with an antibody capable of binding only the denatured state of the target protein;

(ii) incubating the target protein in the presence of each of said test ligands and an antibody directed against only the native state of the target protein; and (iii) determining the presence of the target protein bound or remaining unbound to the surface.

10. The method of claim 6, wherein the determining step comprises the steps of:

(i) coating a surface with an antibody capable of binding the native state of the target protein;

(ii) incubating the target protein in the presence of each of said test ligands and an antibody directed against the denatured state of the target protein; and (iii) determining the presence of the target protein bound or remaining unbound to the surface.

11. The method of claim 6, wherein the determining step comprises the steps of:

(i) coating a surface with an antibody capable of binding the denatured state of the target protein;

(ii) incubating the target protein in the presence of each of said test ligands and an antibody directed against only the folded state of the target protein; and (iii) determining the presence of the target protein bound or remaining unbound to the surface.

12. The method of claim 2 wherein the determining step comprises determining the amount of target protein bound to a molecular chaperone protein or not bound to a molecular chaperone protein.

13. The method of claim 12, wherein the determining step comprises the steps of:
   (i) coating a surface with a molecular chaperone protein;
   (ii) incubating the target protein and each of said test ligands on the coated plate; and
   (iii) determining the amount of the target protein bound to or remaining unbound to the surface.

14. The method of claim 12, wherein the determining step comprises the steps of:
   (i) coating a surface with the target protein in a denatured state;
   (ii) incubating a purified form of the target protein in the presence of each of said test ligands and a molecular chaperone protein on the surface; and
   (iii) determining the amount of the molecular chaperone protein remaining unbound to or binding to the surface.

15. The method of claim 12, wherein the determining step comprises the steps of:
   (i) coating a surface with antisera capable of binding to the folded target protein;
   (ii) incubating the target protein in the presence of a molecular chaperone and each of said test ligands on the surface; and
   (iii) determining the amount of the target protein binding to or remaining unbound to the surface.

16. The method of claim 2 wherein the determining step comprises determining differential formation of aggregated protein using a method selected from the group consisting of:
   (i) measuring the amount of aggregated protein;
   (ii) measuring the amount of soluble protein and measuring the rate of formation of aggregated protein.

17. A method for rapid, large-scale screening to identify a ligand that binds predetermined target protein, comprising the steps of:
   (a) selecting as test ligands a plurality of compounds not known to bind m the target protein;
   (b) incubating each of said test ligands and the target protein under conditions appropriate for the target protein to unfold to a measurable extent, thereby producing a test combination;
   (c) incubating the target protein as in step (b), but in the absence of a test ligand, to produce a control combination;
   (d) determining the extent to which the target protein occurs in the folded state, the unfolded sate or both in the test combination and in the control combination;
   (e) comparing the determination made in step (d) between the test and control combinations, wherein if the target protein is present in the folded state to a greater extent in the test combination than in the control combination, the test ligand is a ligand that binds to the target protein; and
   (f) repeating steps (b)–(e) with a plurality of said test ligands until a ligand that binds to the target protein is identified.

* * * * *